US006530922B2

(12) United States Patent
Cosman et al.

(10) Patent No.: US 6,530,922 B2
(45) Date of Patent: *Mar. 11, 2003

(54) CLUSTER ABLATION ELECTRODE SYSTEM

(75) Inventors: Eric R. Cosman, Belmont, MA (US); William J. Rittman, III, Lynnfield, MA (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/491,748

(22) Filed: Jan. 27, 2000

(65) Prior Publication Data

US 2002/0111615 A1 Aug. 15, 2002

Related U.S. Application Data

(63) Continuation of application No. 08/900,682, filed on Jul. 25, 1997, which is a continuation-in-part of application No. 08/634,005, filed on Apr. 15, 1996, which is a continuation-in-part of application No. 08/562,986, filed on Nov. 24, 1995, which is a continuation-in-part of application No. 08/433,799, filed on May 4, 1995, application No. 09/491,748, which is a continuation-in-part of application No. 08/661,802, filed on Jun. 11, 1996, which is a continuation of application No. 08/167,676, filed on Dec. 15, 1993.

(51) Int. Cl.[7] .............................................. A61B 18/04
(52) U.S. Cl. .............................. 606/34; 606/32; 606/41
(58) Field of Search .............................. 606/34, 32, 41, 606/45–50; 607/96, 100–101, 104, 113, 154, 156

(56) References Cited

U.S. PATENT DOCUMENTS

| 5,403,311 A | * | 4/1995 | Abele et al. ................... 606/49 |
| 5,472,441 A | * | 12/1995 | Edwards et al. ............... 606/41 |
| 5,490,850 A | | 2/1996 | Ellman et al. |
| 5,536,267 A | * | 7/1996 | Edwards et al. ............... 604/22 |
| 5,868,740 A | * | 2/1999 | LeVeen et al. ................. 606/41 |
| 6,053,912 A | * | 4/2000 | Panescu et al. ............... 606/31 |
| 6,059,780 A | * | 5/2000 | Gough et al. .................. 606/41 |
| 6,337,998 B1 | * | 1/2002 | Behl et al. ..................... 606/41 |

FOREIGN PATENT DOCUMENTS

| WO | WO 96/04860 | 8/1995 |
| WO | WO 96/29946 | 3/1996 |
| WO | WO 96/39914 | 5/1996 |

OTHER PUBLICATIONS

International Search Report.
International Preliminary Examination Report.

* cited by examiner

Primary Examiner—Michael Peffley
Assistant Examiner—Peter J Vrettakos

(57) ABSTRACT

A multiplicity of high frequency electrodes in a cluster configuration may be inserted into tissue of a patient's body for producing heat ablation of abnormal tissue such as a tumor. The electrodes are connected coherently to the voltage output of a high frequency generator. An enlarged ablation volume is accomplished by the electrode cluster with reduced risk of hemorrhage because of the smaller diameter of the individual electrodes of the cluster. The electrodes terminate in conductive tips, which are cooled by a fluid coolant to further facilitate enlarged ablation volumes. Very large ablation volumes are accomplished by this process and apparatus. Various cluster electrode configurations may be adapted to meet specific clinical requirements.

15 Claims, 5 Drawing Sheets

CLUSTER ABLATION ELECTRODE SYSTEM

CROSS REFERENCE TO RELATED APPLICATIONS

This application is a continuation of Ser. No. 08/900,682 filed Jul. 25, 1997 which is a continuation-in-part of application Ser. No. 08/634,005 filed on Apr. 15, 1996, ABN and entitled "COOL-TIP ELECTRODE THERMOSURGERY SYSTEM," which is a continuation-in-part of application Ser. No. 08/562,986 filed on Nov. 24, 1995, and entitled "COOL-TIP RADIOFREQUENCY THERMOSURGERY ELECTRODE SYSTEM FOR TUMOR ABLATION," which is a continuation-in-part of application Ser. No. 08/433,799 filed on May 4, 1995, and entitled "A COOLED RADIO FREQUENCY ELECTRODE SYSTEM FOR HEAT ABLATION IN THE BODY," now abandoned, and also a direct continuation-in-part of application Ser. No. 08/433,799 filed on May 4, 1995, and entitled "A COOLED RADIO FREQUENCY ELECTRODE SYSTEM FOR HEAT ABLATION IN THE BODY," now abandoned. This application is also a continuation-in-part of application Ser. No. 08/661,802 filed on Jun. 11, 1996, and entitled "HIGH FREQUENCY THERMAL ABLATION OF CANCEROUS TUMORS AND FUNCTIONAL TARGETS WITH IMAGE DATA ASSISTANCE," which is a continuation of application Ser. No. 08/167,676, filed Dec. 15, 1993, and entitled "HIGH FREQUENCY THERMAL ABLATION OF CANCEROUS TUMORS AND FUNCTIONAL TARGETS WITH IMAGE DATA ASSISTANCE." Both the co-pending applications from which the present application directly claims priority, are incorporated herein by reference.

FIELD OF THE INVENTION

This invention relates generally to advances in medical systems and procedures for prolonging and improving human life. More particularly, this invention relates to an improved system and method, including clusters or multiple coherent arrays of radiofrequency electrodes configured in an arrangement for producing large ablation volumes in tissue containing abnormalities such as cancerous tumors.

BACKGROUND OF THE INVENTION

The use of radiofrequency electrodes for ablation of tissue in a patient's body is known. In a typical situation, a radiofrequency electrode comprising an elongated, cylindrical shaft with a portion of its external surface insulated is inserted into the patient's body. The electrode typically has an exposed conductive tip, which is used to contact body tissue in the region where the heat lesion or ablation is desired. The electrode is connected to a radiofrequency power source, which provides radiofrequency voltage to the electrode, which transmits the radiofrequency current into the tissue near its exposed conductive tip. This current usually returns to the power source through a reference electrode, which may comprise a large area conductive contact connected to an external portion of the patient's body. This configuration has been described in articles, as for example, a research paper by Cosman, et al., entitled "Theoretical Aspects of Radiofrequency Lesions in the Dorsal Root Entry Zone," *Neurosurgery*, December 1984, Vol. 15, No. 6, pp 945–950, and a research paper by Goldberg, et al. entitled "Tissue Ablation with Radiofrequency: Effective Probe Size, Gauge, Duration, and Temperature and Lesion Volume" *Acad Radio.*, 1995, Vol. 2, No. 5, pp 399–404. Radiofrequency lesion generators and electrode systems such as those described above are commercially available from Radionics, Inc., located in Burlington, Mass.

To enlarge ablation volumes, electrodes with curved conductive tips have been proposed. Such tips are injected from a cylindrical electrode placed near the targeted or desired tissue volume to produce an off-axis, curved arc within the targeted or desired tissue. In this way, off-axis ablation volumes may be produced away from the central axis of the inserted cannula. The off-axis lesions produced by these off-axis radiofrequency electrodes enlarge the lesion volume away from an axially symmetric, exposed electrode tip. One example of this type of an off-axis electrode is the Zervas Hypophysectomy Electrode available from the company Radionics, Inc., located in Burlington, Mass. Another example of this type of an off-axis electrode is the multiple side-emitting, off-axis electrode made by Radiotherapeutics, located in Mountainview, Calif. The multiple electrode elements range in curved arcs at various azimuthal angles. By making an umbrella of off-axis tip extensions at various azimuthal angles relative to a central insertion cannula, an enlarged lesion volume can be produced. Disadvantages of irregular heat ablation shapes and large central cannula sizes are discussed below.

Also, pairs of electrodes have been inserted into the body in a bipolar configuration, typically in parallel pairs held close to each other. Examples of such bipolar configurations are available from the company Elekta AB, located in Stockholm, Sweden. In such bipolar configurations, one electrode serves as a source and the other serves as a sink for the radiofrequency current from the RF generator. In other words, one electrode is disposed at the opposite voltage (pole) to the other so that current from the radiofrequency generator is drawn directly from one electrode to the other. The primary purpose of a bipolar electrode arrangement is to insure more localized and smaller heat ablation volumes. With such configurations, the ablation volume is restricted to the region between the bipolar electrodes.

Hyperthermia is a method of heating tissue, which contains a cancerous tumor, to thermally non-lethal levels, typically less than 45 degrees Centigrade combined with irradiation of the tissue with X-rays. Such application of mild non-lethal heating in combination with radiation by X-rays enhances destruction of cancer cells while sparing the normal cells from being killed. For hyperthermia, multiple arrays of high frequency electrodes are implanted in tumors. The electrodes are typically placed in a dispersed fashion throughout the tumor volume to cover the tumor volume with uniform heat, which is below the lethal 45 degree level. The electrodes are sequentially applied with high frequency voltage so that each electrode heats in sequence its neighborhood tissue and then. shuts off. Then, the next electrode does the same in a time series. This sequence of cycling the voltage through the electrodes continues at a prescribed frequency and for a time period ranging anywhere from minutes to hours. The primary objective of hyperthermia is not to fully ablate tumors by outright heat destruction of the cancerous tumor. On the contrary, its objective is to avoid temperatures above 45 degrees C. anywhere in the treatment volume. The article by Melvin A. Astrahan entitled "A Localized Current Field Hyperthermia System for Use with 192-Iridium Interstitial Implants," in *Medical Physics*, 9(3), May/June 1982, describes the technique of radiofrequency hyperthermia.

Electrodes with cooled conductive tips have been proposed by Goldberg, et al., in their article referenced above. With cooling, electrode tips generally produce larger lesion volumes with radiofrequency electrodes, which are not cooled.

The electrode systems discussed above are limited by the practical size of lesion volumes they produce. For example, standard single cylindrical electrodes, with cool tips, as described above, make lesion volumes up to 3 to 4 cm in diameter in living tissue such as the liver using cannulae of 1 to 2 mm in diameter and several centimeters exposed tip length. The umbrella lesions made by multiple side-emerging, exposed tips, also produce lesion sizes of 3 to 4 cm volume diameter. A severe hazard of multiple extrusion of side-outlet electrodes is that it produces hemorrhaging by the multiple passes of the side outlet electrodes near the central cannula. Also, at the periphery of such side-emitting electrode lesions, irregularities and undulations in lesion shape and inhomogeneities in temperature around the side-emitted electrode tips produce hot and cold spots over the lesion volume. These may cause focal boiling and charring of tissue with unpredictable and dangerous consequences. For example, consider a large tumor of about 3 to 4 cm diameter in the liver. In such an example, there is a further risk that such undulations and variations in the shape of the periphery of the heat ablation zone would cause portions of the cancerous tumor to be missed by the heat ablation, which of course, would result in continued tumor growth and progression of cancer. Further, a single central cannula, which has one or many side-emitting radiofrequency electrode tips has a diameter, which increases with the number of radiofrequency tips that emerge from it. When the diameter reaches 3 to 4 mm for such a central cannula, there is the disadvantage of increased risk of hemorrhage and/or great pain or discomfort to the patient during insertion of the large central cannula into the tissue.

Thus, a configuration of radiofrequency electrodes, which can accomplish ablation volumes in the range of 4 to 6 cm diameter or greater for the purpose of adequately treating large cancerous tumors in the body are necessary to effectively destroy the tumor and combat cancerous cells from spreading. It is further necessary that such an electrode system involve a simple geometry, reduced numbers of tissue insertions, simple planning of needle placement, and simple planning of heat ablation geometry and distribution. An electrode system, which can be easily inserted into an organ or through the skin with minimal risk of hemorrhage and discomfort to the patient. An electrode system and method, which produces minimal lesion inhomogeneities to avoid complications of boiling and charring, and which avoids the inadvertent missing of outlying colonies of cancer cells in an irregular tumor is not only desirable, but necessary.

SUMMARY OF THE INVENTION

The present invention is directed to a system and procedure for using clusters or multiple arrays of electrodes arranged in a configuration for producing large ablation volumes in body tissue for effectively treating diseases such as cancer.

In one embodiment of the present invention, a parallel array of rigid, straight radiofrequency electrodes is inserted into body tissue that includes a cancerous tumor. The electrodes may be rigid metal tubes insulated over a portion of their length, except for their exposed conductive tips, which are shaped to terminate in pointed, tissue-piercing ends. The electrodes are configured in a cluster or array.

In one embodiment, the cluster is configured such that the electrode tips lie in close proximity to each other. Each electrode of the cluster is coupled to a radiofrequency generator located external to the patient's body so that the conductive tips of each electrode in the cluster is raised to the same radiofrequency voltage. In this embodiment, the conductive electrode tips represent equipotential surfaces, which are positioned in proximity to each other. They create an effectively larger equipotential electrode due to the coherent voltage applied to all of them. This large effective electrode produces a larger ablation volume. Also, in some embodiments, by cooling fluid circulating within each of the electrodes in the cluster larger ablation volumes are formed. Lesion volumes of 4 to 6 cm diameter are easily accomplished, which is advantageous in many clinical situations, especially where curtailing large areas of cancer cells is necessary.

Contrary to existing electrode configurations and techniques, which propose inserting one large electrode into body tissue, thereby often causing severe hemorrhage, the present system of coherent cluster electrodes inserts into body tissue, multiple independent rigid electrode shafts of the cluster, each of appropriate small diameter, which reduces the risk of hemorrhage. The problem of irregular lesion ablation zones and inhomogeneities of ablation regions associated with prior side-emitting electrodes is also avoided by the coherent cluster electrodes of the present invention.

By applying the same radiofrequency voltage simultaneously to a cluster of electrodes accomplishes heat ablation effects vastly different from and far superior to heat ablation effects accomplished by applying the same voltage sequentially or serially to the same number of single electrodes (not in a cluster). With the coherent cluster electrode of the present invention, where the same or nearly the same radiofrequency voltage is applied to all the electrodes, the equipotential surfaces formed around the cluster are different from equipotential surfaces for individual electrodes of the cluster raised separately or sequentially to the desired RF potential. In some cases this may result in an heat ablation effect similar to that accomplished by using a single larger electrode. The present invention enables larger amounts of power to be deposited into the desired tissue area before hot spots occur around each electrode and raise the tissue temperature towards its boiling point. Furthermore, by cooling each of the electrodes, a larger withdrawal of radiofrequency heating power from the tissue proximate to the electrodes is accomplished when compared with cooling of only a single radiofrequency electrode within the cluster. Both coherent RF voltage application and cooled electrodes increase the lesion size associated with the cluster of RF electrodes.

Another advantage of the present invention is that by using the present cluster electrode system, the shape of the ablation volume may be controlled such that it is uniform at its outer margins. By way of one example, for a large cancerous tumor, which is irregular in shape, an ablation volume of sufficiently larger size may be formed to better ensure that the entire tumor is engulfed or consumed by the resulting heat lesion to destroy it completely. Planning where to place the coherent cluster electrode system is simpler than planning where multiple radiofrequency electrodes should be placed over an extended volume of tissue.

Yet another advantage of the coherent cluster electrode system of the present invention is that in accordance with one embodiment it enables all its electrodes to be inserted in unison and in a known geometric relationship to one another. In one embodiment, each electrode may be configured with a small shaft with a pointed, self-penetrating tip. Accordingly, the chance of a hemorrhage occurring from a multiple cluster of such smaller electrodes is less likely than with a single electrode of larger diameter. Even if the cluster of electrodes is not inserted in a precisely parallel fashion, the effect of their coherence in making a larger lesion volume is still effective.

The present coherent cluster of electrodes may configured in various ways, with or without cooling, to address specific clinical needs.

BRIEF DESCRIPTION OF THE DRAWINGS

Further features and advantages of the invention will become readily apparent from the following specification and from the drawings, in which.

DESCRIPTION OF SOME PREFERRED EMBODIMENTS OF THE INVENTION

The prior applications from which priority is claimed are incorporated herein by reference. Also, the published papers by Cosman, et al., entitled "Theoretical Aspects of Radiofrequency Lesions in the Dorsal Root Entry Zone," and Goldberg, et al., entitled "Tissue Ablation with Radiofrequency: Effective Probe Size, Gauge, Duration, and Temperature and Lesion Volume," mentioned above are incorporated herein by reference.

Figure 1:
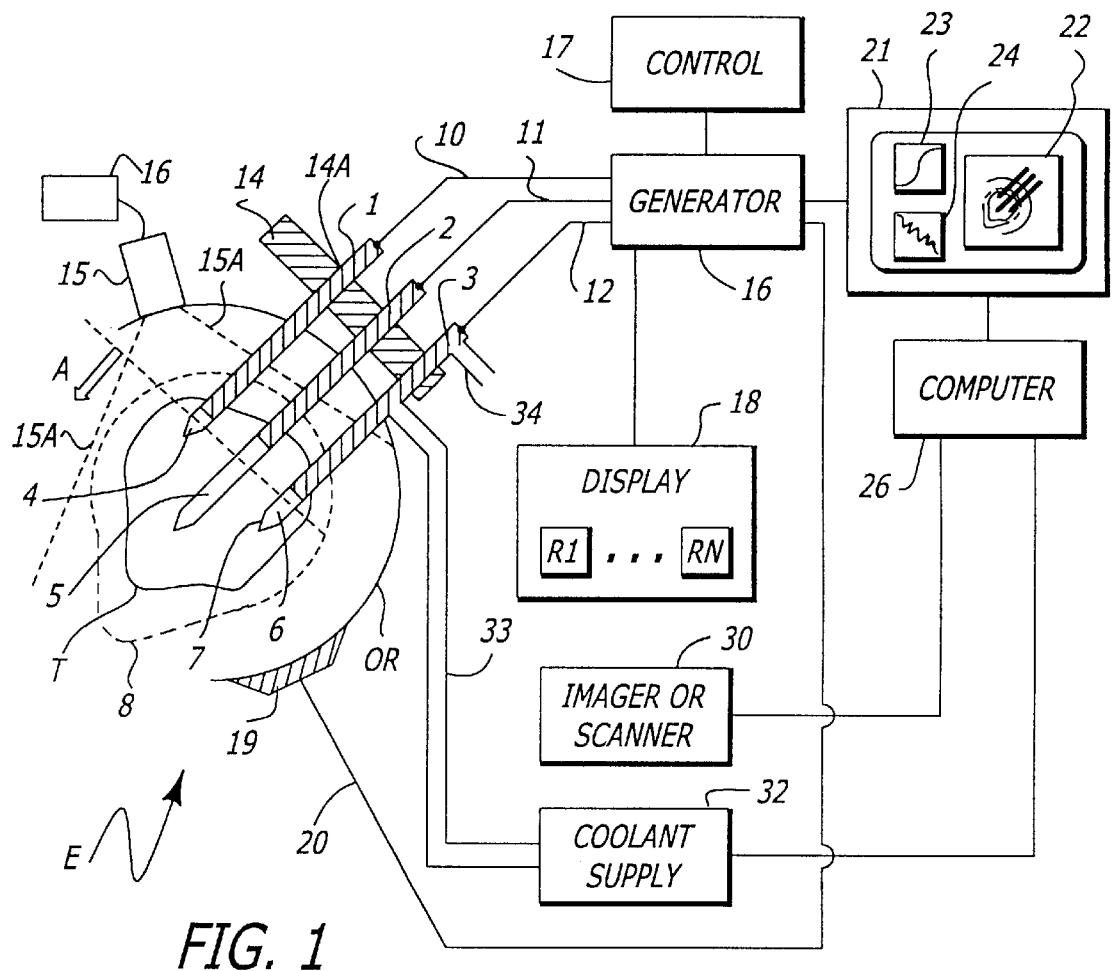
FIG. 1 shows schematically multiple radiofrequency (RF) electrodes positioned in a patient's organ for producing heat ablation of a targeted tissue area in accordance with the coherent cluster electrode system of the present invention.

Referring now to FIG. 1, one embodiment of the coherent cluster electrode in accordance with the present invention referenced by letter E is generally illustrated. The cluster electrode system E comprises a plurality of electrodes 1, 2, and 3, that are inserted into an organ OR, which may represent any organ in a human body. Their distal tips 4, 5, and 6, respectively, are uninsulated and conductively exposed so that electrical currents induce heating within the tissue or organ OR. A targeted volume of tissue T is shown in sectional view, which may represent, for example, a tumor or other abnormality in a human body.

The electrodes 1, 2, and 3, are coupled by wires or cables 10, 11, and 12, as shown, to a generator 16. The generator 16 may be a radiofrequency or high frequency type of generator, such as one available under Model No. RFG-3C from Radionics Inc., located in Burlington, Mass. The generator 16 has control elements, illustrated generally by block 17, which may, for example, increase the radiofrequency power output to the electrodes, control temperature when the cluster electrode system E or satellite sensors comprise temperature sensors, monitor or control impedance, power, current, voltage, or other output parameters. The generator 16 may include a display provision, illustrated by block 18, within it or as a separate system, for providing a display of heating parameters such as temperature for one or more of the electrodes, impedance, power, current, or voltage of the radiofrequency output. Such individual display readings are illustrated by the reference letters R1, . . . to RN.

A reference electrode 19 is also shown, which may be placed in contact with the skin of a patient or the external surface of the organ OR with a connection 20 to the generator 16. In one embodiment, this serves as a path for return current from the generator 16 through the electrodes 4, 5, and 6. More details on the heating mechanism are discussed in the papers by Cosman, et al., and Goldberg, et al., the content of which is incorporated herein by reference.

The electrodes 1, 2, and 3 in accordance with one exemplary embodiment, comprise rigid shafts, which may be easily urged into the body tissue. They terminate in tissue-penetrating pointed tips 7 on electrode ends 6. They have a portion of their external shaft surface of insulated material indicated by the hatched line areas on electrodes 1, 2, and 3. The distal tip referenced by 4, 5, and 6 for each electrode comprise conductive metal and are connected through the shafts 1, 2, and 3 to the connection cable 10, 11, and 12 respectively, and thereby to the generator output source 16.

By way of one specific example, the generator 16 may be a radiofrequency generator with frequency between about 100 kilo Hertz to several hundred mega Hertz. An example of such a generator is the lesion generator available from Radionics, Inc., of Burlington, Mass. It may have power output ranging from several watts to several hundred watts, depending on the clinical application.

According to the present invention and illustrated in FIG. 1, the electrodes 4, 5, and 6 may be raised to the same radiofrequency voltage potential from the generator 16. The cluster of electrodes thus becomes, in effect, a larger, coherent electrode comprising the individual electrode tip elements 4, 5, and 6. Thus, its heating effect is similar to that accomplished by one large single electrode. With the cluster electrode system of the present invention, the individual electrodes 4, 5, and 6 cause less traumatic and do not induce hemorrhaging when they penetrate the organ OR because of their smaller size. Yet when they are connected to a coherent, parallel voltage level, they represent an effectively much larger electrode. In this way, larger heat volumes, and therefore ablation sizes, may be achieved.

As an illustration, in FIG. 1 the targeted volume is represented in sectional view by the line T. Consider that it is desired to ablate the targeted region T by fully engulfing it in a volume of lethal heat elevation. The targeted area T may be, for example, a tumor which has been detected by image scanner 30. CT, MRI, or ultrasonic image scanners may be used, and the image data transferred to computer 26. As an alternate example, an ultrasonic scanner head 15 may be disposed in contact with OR to provide an image illustrated by lines 15A. Data processor 16 may be connected to display devices to visualize the tumor T and/or ablation zone 8 in real time during the ablation procedure. The image representation of the scan may be displayed on display unit 21, which may, for example, be a CRT screen. Slice renderings through the organ OR may be displayed in window 22 to represent the size and position of targeted volume T. Placement of the electrodes 4, 5, and 6 may be predetermined based on such image data as interactively determined by real-time scanning of organ OR. The electrodes are inserted into the tissue by freehand technique by a guide block with multiple hole templates, or by stereotactic frame or frameless guidance as, for example, by stereotactic instruments made by Radionics, Inc., of Burlington, Mass. A stereotactic guide is shown schematically by element 14. Guide holes such as 14A for electrode 1 aim it to the desired targeted position based on image data.

In accordance with the present invention, a cluster of electrodes 1, 2, and 3 are connected to the same radiofrequency voltage from generator 16. They thus will act as an effectively larger electrode. Their relative positions and orientations enable different positive shapes and sizes of ablation volumes to be made. For example, in FIG. 1 the dashed line represents the ablation isotherm in a sectional view through organ OR. Such an ablation isotherm may be the surface achieving temperatures of approximately 50 degrees or greater. At that temperature range, sustained for about 30 seconds to several minutes, tissue cells will be killed or ablated, in accordance with the paper of Cosman, et al., referred to above. The shape and size of the ablation volume illustrated by dashed line 8 may accordingly be controlled by the configuration of the electrode cluster, the geometry of the exposed tips 4, 5, and 6, the amount of RF power applied, the time duration that the power is applied, cooling of the electrodes, and so on.

Figure 2A:
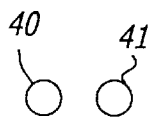
FIGS. 2a, 2b, 2c, 2d, 2e, and 2f illustrate diagrammatically by way of example, various configurations in which the electrodes may be arranged in the coherent cluster electrode system in accordance with the present invention.

Referring to FIG. 2a, 2b, 2c, 2d, 2e, and 2f, various cross-sectional representations of embodiments of the cluster electrodes in accordance with the present invention are shown. The configuration of electrodes is shown as viewed in planar section A, illustrated in FIG. 1. Referring to FIG. 2a, two electrode shafts, 40 and 41, are depicted. They may be circular metal tubes and may be spaced apart and located at various distances. For example, the shaft diameters of elements 40 and 41 could range from a fraction of a millimeter to several millimeters in diameter. They could be contiguous with substantial tangency of their shafts when the shafts are very close together, or they could be separated by several millimeters, depending on clinical needs.

Figure 2C:
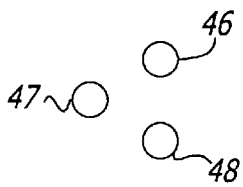
Figure 2E:
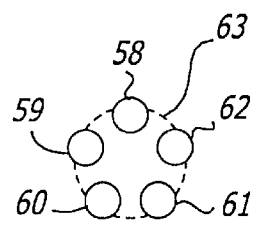
Figure 2B:
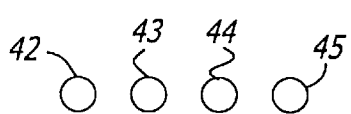

Referring to FIG. 2b, a multiplicity of such shafts in sectional view A are shown. Electrodes 42, 43, 44, and 45 may be circular diameter metal tubes, and they could be placed in a substantially linear array as shown. Such a nearly linear array may be useful in various clinical applications. For example, if an effectively planar array of electrode tips is needed within the bodily tissue, such a nearly linear array is helpful. The spacing between the electrodes may be equal or different, depending on the clinical need. The arrangement of electrodes need not be exactly linear, as shown in FIG. 2b. The electrodes may be inserted in a curved pattern depending on the shape of the heat ablation required or the anatomical objects that may or may not be encountered during electrode insertion.

FIG. 2c shows a cluster electrode system in which the electrode shafts are in a non-linear or geometric pattern. In this case, there are three electrodes, 46, 47, and 48, in a triangular pattern. The distance between the individual electrode elements of the trident elements may be variable, ranging from 0 to several millimeters, or even centimeters. The diameter of the shafts may also range from a fraction of a millimeter up to several millimeters or more.

Figure 2D:
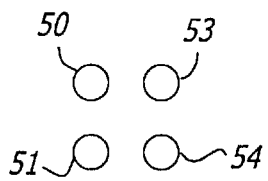

FIG. 2d illustrates a quadruple cluster electrode where the electrodes are in a rectangular or quadrilateral pattern. The electrodes 50, 51, 53, and 54 are placed on nearly a square in FIG. 4d to accommodate a geometric pattern according to clinical needs.

FIG. 2e illustrates a five-fold cluster electrode in a pentagon pattern. Electrodes 58, 59, 60, 61, and 62 may be clustered in a nearly circular locus of points or in an ellipsoidal geometry to accommodate clinical needs.

More electrodes in other geometric patterns or configurations to address particular needs may be arranged in accordance with the present invention. Several or all of the electrodes in each pattern may be connected to the same high frequency potential, yielding an effective equipotential surface for the cluster electrodes to simulate equivalency of a much larger single electrode. In each of the examples, also, the electrodes may be cooled by a coolant, such as chilled circulating saline, within them. Thereby, the cluster electrode represents an effectively larger, cooled radiofrequency structure. With adaptions a much larger radiofrequency ablation may be accomplished. Multiplicities of cluster electrodes may also be implemented for other geometric or clinical advantages.

Figure 2F:
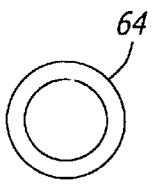

In one embodiment of the invention, each of the radiofrequency electrodes is connected to the same high frequency potential. As in the examples of FIG. 2, the effective diameter of the radiofrequency electrode system increases in a coherent way. For example, in FIG. 2e if the electrodes 58, 59, 60, 61, and 62 are all maintained at the same radiofrequency potential, they then become similar in heating effect to a single larger radiofrequency electrode. In the configuration of FIG. 2e, for example, the spacing between the electrodes is not substantially larger than the diameter of the individual electrode elements, and the coherent equipotential effect of the cluster may be simulated by a single circular electrode having a diameter equal to that of the dashed circular line 63. At distances away from the cluster, the heating effect for the five individual RF electrodes begins to approach the heating effect from a single circular electrode illustrated by the dashed line 63. This, therefore, may be equivalent for RF thermal ablation to a solid circular electrode, as illustrated in FIG. 2f, which in sectional view is shown as the circular tube 64.

The use of a multiplicity of N electrodes increases the overall conductive exposed tip area by which to send RF current for heating into the tissue. This increases the heating power that may be delivered and thus increases the size of the ablation volume possible.

The cooling capacity of a multiplicity of N electrodes also increases as the number N increases. Increasing the number of electrodes increases the cooling surface area near the electrode cluster. Thus, the heat sinking effect from a cluster of electrodes is greater than the heat sinking effect from a single electrode element of the cluster. This enables the lesion size to be expanded accordingly.

As an example of specific embodiments of the cluster electrodes of FIG. 2, the individual electrode shafts may be in the range of 0.5 to 3.0 mm. They may be arranged in a cluster of two or more electrodes which are essentially parallel, rigid shafts. The cluster of exposed distal tips in sectional view may be included in a circle of 3, 5, 10, 15, 20, 25 millimeters or larger. The proximal ends of the shafts may be fixedly positioned in a hub-like structure. Electrical and cooling wires and tubes may access the individual electrode through the hub.

Figure 3:
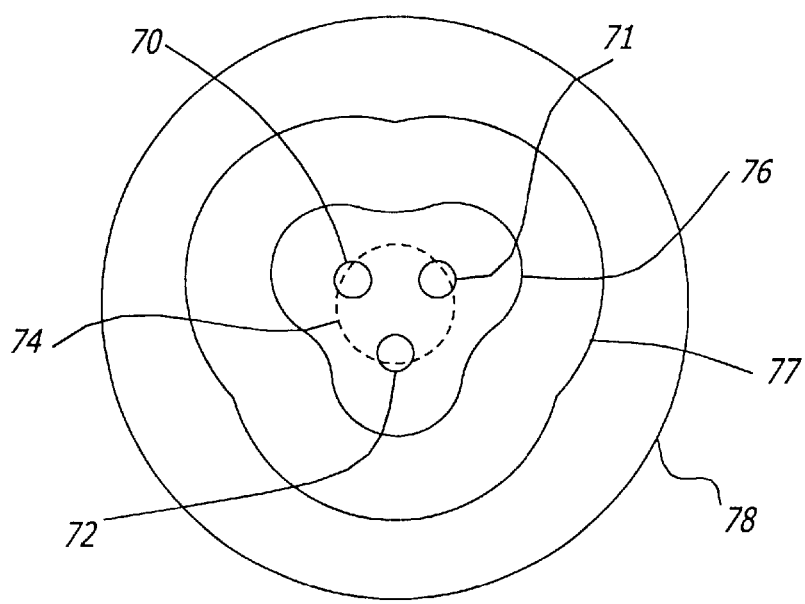
FIG. 3 illustrates schematically equipotential lines associated with one embodiment of a coherent cluster electrode system in accordance with the present invention having three electrodes.

By way of further explanation, FIG. 3 shows another sectional view of a triple electrode cluster through, for example, sectional slice A in FIG. 1. The electrode cross-sections are illustrated by elements 70, 71, and 72, which, for example, may be circular metal tubular shafts of the electrode. The section is through the exposed tip portion of the electrodes, as illustrated in FIG. 1. By way of illustration, some equipotential surfaces through Section A are qualitatively illustrated by the lines 76, 77, and 78. Equipotential surfaces are locuses of constant potential (or voltage) which are established by raising the electrodes 70, 71, and 72 to a common radiofrequency voltage. The equipotential surfaces define also the electric field created by the radiofrequency voltage. The electric field, in turn, determines the radiofrequency current within the tissue, and this gives rise to the frictional heat dissipation that causes the heating power deposition around the electrode. For reference, the theory of electric fields and potentials is described in the textbooks *Electricity and Magnetism* by E. M. Purcell, and *Classical Electrodynamics* by J. D. Jackson; and Electricity and *Magnetism* by J. H. Jeans. The theory of radiofrequency heating may be found in part in the above cited paper by Cosman, et al.

FIG. 3 qualitatively shows that the equipotential lines 76, 77, and 78 approach a circular contour for line 78 as the distance away from the cluster of electrodes increases. The equipotential lines at larger distances begin to approximate the equipotential shapes that would occur for a single, much larger electrode with a shaft diameter as is illustrated by a circle 74. Furthermore, for distances near to the cluster, when the separation of elements 70, 71, and 72 of the cluster is not too great compared to the diameters of the elements 70, 71, and 72 themselves, there is a coherent effect on equipotential surfaces, electric fields, and heating patterns. For instance, in the configuration of FIG. 3, when the elements 70, 71, and 72 are at the same RF potential, the electric potential inside the triple cluster of electrodes is relatively uniform. Therefore the electric field there will be small, and the RF power dissipation inside the electrode cluster pattern is also small. This is not the case if each of the individual electrodes were, for example, powered to the RF potential in a sequential manner (not simultaneously), wherein significant power dissipation would take place in the region inside of the triplet electrodes. There is more uniformity of heating outside the cluster of electrodes by the coherent application of the same radiofrequency voltage to several of the electrode elements of a cluster. This may reduce ablation hotspots, focal boiling, and charring of tissue.

An advantage of a multiplicity of coherent smaller electrodes versus insertion of a single large electrode is that the smaller electrodes will produce less chance of hemorrhage. The arrangement of their geometry may also be tailored to the clinical application. Insertion of several small gauge electrodes is less painful, uncomfortable, and risk-inducing than insertion of one large, equivalent radiofrequency electrode. For example, insertion of a cluster of several 18 gauge or 1.25 mm diameter pointed radiofrequency electrodes into the liver produces very low risk of hemorrhage and low discomfort. Insertion of an equivalent, but much larger single electrode, which may have a diameter of, for example, 0.25" or 6.4 mm, would have a higher risk of hemorrhage and would be very uncomfortable for the patient if the electrode were inserted percutaneously.

It is also noted in FIG. 3 that each of the electrodes 70, 71, and 72 may have coolant fluid such as chilled saline flowing within their tips to cool the entire region near them. The cooling effect enables much larger radiofrequency lesions to be produced in accordance with the parent application referred to above.

Figure 4:
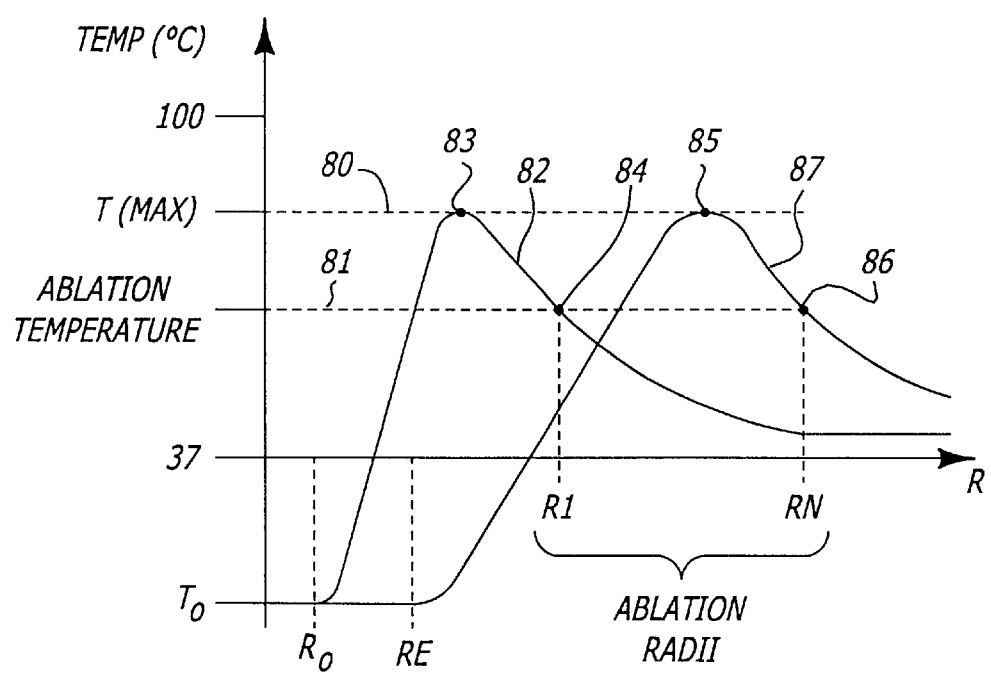
FIG. 4 shows graphical schematic representations of temperature readings versus distance taken from an example of a single radiofrequency electrode and compared with similar readings taken from one embodiment of the coherent cluster electrode system of the present invention.

FIG. 4 illustrates schematically the distribution of heating temperature as a function of the radial distances from the electrode. Curve 82 illustrates the temperature distribution for a single cooled electrode such as electrode 70 in FIG. 3. Its radius of circular section is $R_0$. With cooling circulation within it, the temperature within the electrode is $T_0$. The application of radiofrequency energy to the tissue through the individual electrode produces curve 82. This is the heat distribution from a single electrode, assuming that the other cluster electrodes are not present. The point of maximum temperature corresponds to the dotted line 80. T(MAX) may be selected by the operator, depending on clinical need. The horizontal dotted line 81 corresponds to the temperature at which tissue is killed. This is approximately in the range of 40 to 50 degrees, when sustained for many seconds or minutes. Curve 82 intersects the ablation temperature line 81 at point 84. This would correspond to the nominal radius of an ablation volume indicated by R1.

Still referring to FIG. 4, the curve 87 illustrates schematically a temperature distribution for the cluster of three electrodes, as for example in FIG. 3. The electrodes 70, 71, and 72, for example each having tube radius $R_0$. As described previously, the effective radius RE of the coherent cluster is a nominal radius of the dotted circle 74 in FIG. 3. If all of the electrode cluster elements-70, 71, and 72 are cooled to temperature $T_0$, then within the effective radius RE, the temperature of the tissue would be approximately $T_0$. When radiofrequency voltage is applied to all of the electrodes 70, 71, and 72 simultaneously, a temperature distribution will be formed, illustrated by curve 87. In this case, the curve extends outward to large radii. For an appropriate power, curve 87 will intersect the dashed line 80 for T(MAX) and point 85. This is at a larger radius than the point 83 for a single smaller electrode. Furthermore, the curve 87 intersects the ablation temperature line 81 at point 86. This corresponds to a radius R2, which is greater than the radius R1.

Curve line 87 may be similar to a single radiofrequency electrode with radius RE, internally cooled to temperature $T_0$ The temperature distribution within the cluster of electrodes is similar to that for a single cooled shaft, and the temperature distribution outside of the cluster electrode simulates that for a single larger radius electrode. This coherent cluster temperature distribution is substantially different from the distribution one would achieve by applying radiofrequency and cooling to the individual cluster elements (such as 70, 71, and 72 in FIG. 3) in an individual, separated, sequential manner. The coherent nature of the cluster electrode is an advantage to achieving a larger heat ablation.

To give a specific example, a triad cluster is constructed of three rigid metal electrodes, each having a shaft of circular cross-section with diameter of about 1.2 mm. Each electrode shaft is insulated except for a two centimeter exposed tip. The three tips are sharpened to pierce skin and tissue. At the distal end of the triad cluster electrode, the electrode tips are held in essentially parallel orientation and in close proximity to each other by fixing the opposite proximal ends of the individual electrode shafts in a hub. The central axes of the tips are positioned on an equilateral triangle with separation distance between the tips being approximately 5 to 7 mm. Cooled saline of approximately zero degrees centigrade is circulated through all three electrodes to enable a larger heat lesion to be made.

The electrode cluster is inserted percutaneously and in unison into the liver of a living patient under CT and ultrasound guidance. The 1.2 mm diameter of the individual shafts enable this to be done easily and without hemorrhage or discomfort to the patient. The electrodes were all connected to the same RF voltage output of an RF generator. The application of about 2000 milliamperes of total current to the electrode triad from a radiofrequency generator of 500 KiloHertz frequency for a duration of 12 minutes produced an ablation volume in the liver of 5 to 6 centimeters diameter. This destroyed a 2 to 3 centimeter diameter cancerous tumor within the liver with minimal discomfort for the patient and no significant negative side effects. This is compared to typical ablation diameter of about 3 centimeters when only one cooled electrode of the cluster is used. The equipotential triad cluster electrode produces a much larger lesion volume than produced by individually sequenced RF voltages applied to the three electrodes of the triad.

Figure 5:
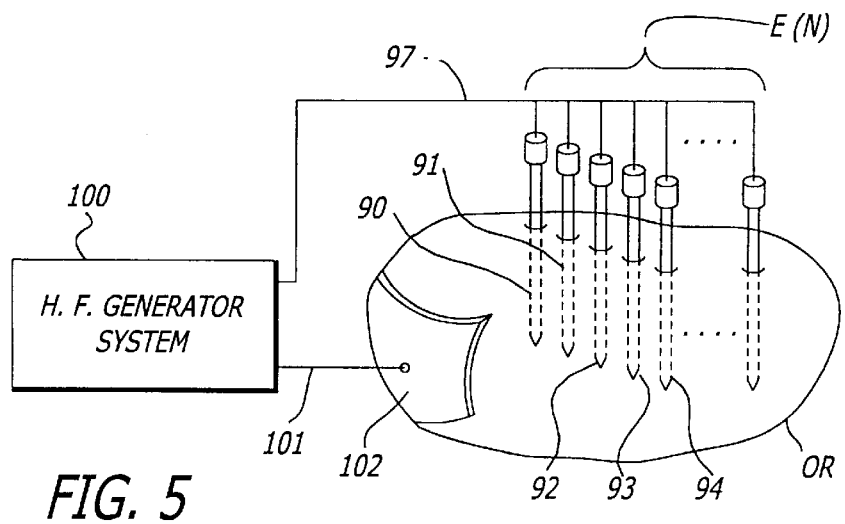
FIG. 5 shows another embodiment of the coherent cluster electrode system in accordance with the present invention.

Referring to FIG. 5, a schematic diagram of another embodiment of the present invention is shown. A series E(N) of N electrodes 90, 91, 92, 93, 94, . . . is shown inserted into organ or bodily element OR. These electrodes may be, for example, metal shafts with an insulated portion, except for an exposed distal tip, as described above. They may have self-penetrating or tissue-piercing, pointed tips. They may be placed in a nearly parallel array so as to present an area-like electrode configuration. This would have a similar effect as a plate-like electrode or a continuous equipotential surface. A connection 97 is made to all of the electrodes 90, 91, . . . from the generator system 100. System 100 may comprise a generator, control, coolant supply, etc., as described above. Separate elements for cooling some or all of the electrodes may be present. A reference area electrode 102 is shown contacting a surface of the organ OR. It is connected by element 101 to the system 100 which may act to return radiofrequency current to the power generator 100 or cooling fluid if area electrode 102 is also a cooled type.

Such a configuration may be clinically useful if a large volume or block of tissue is to be ablated. For example, if the electrodes 90, 91, 92 . . . are inserted in a nearly parallel array in an organ such as the liver, and a reference electrode such as 102 is a plate electrode placed on the surface of the liver roughly parallel to the electrode array E(N), then an effectively "parallel plate" electrode configuration is achieved. In that case, a relatively uniform and large block of ablative heating volume may be induced between the electrode array E(N) and the plate electrode 102. Within that volume, a cancerous tumor or other tissue abnormality, which is desired to be ablated, would be completely destroyed.

Larger ablation volumes may be induced than would otherwise be induced with a single electrode element or by connecting the individual electrodes in sequence to the radiofrequency potential in contrast to connecting them in parallel. The interstitial electrodes may be placed in other than a parallel configuration. They may be put in a curved array or circular array to achieve other geometries of the electrode arrays E(N) suitable to the clinical need.

Figure 6:
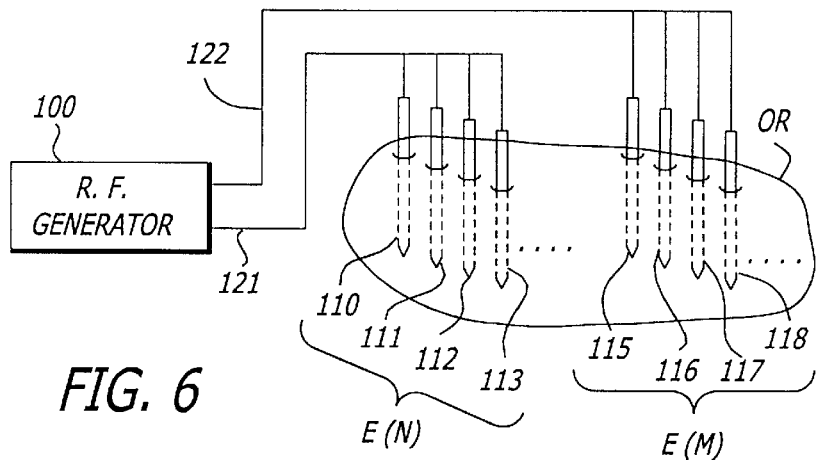
FIG. 6 shows yet another embodiment of the coherent cluster electrode system in accordance with the present invention, comprising a set of parallel, multiple electrodes used in a bipolar arrangement.

Referring to FIG. 6, yet another embodiment of the present invention is shown. In this case, a first cluster E(N) of N electrodes 110, 111, 112, 113 . . . is inserted into organ OR. A second cluster E(M) of M electrodes, indicated by 115, 116, 117, 118 . . . , is inserted into OR. The two clusters, for illustration are shown substantially parallel to one another. Thus each cluster simulates a parallel plate geometry. The electric field will pass in the tissue of organ OR between the two electrode clusters similar to an electric field between two parallel plates of a capacitor. The heat ablation of the tissue is likewise concentrated between the cluster electrode arrays.

Connection 121 connects the individual electrodes in the cluster E(N), and connection 122 connects the individual electrodes in the cluster E(M) to the source of high frequency power represented by generator 100. Thus, current between the electrode arrays passes through the bodily tissue in organ OR between the cluster arrays. The individual element in the array could also be cooled, as cited in FIG. 1.

Figure 7:
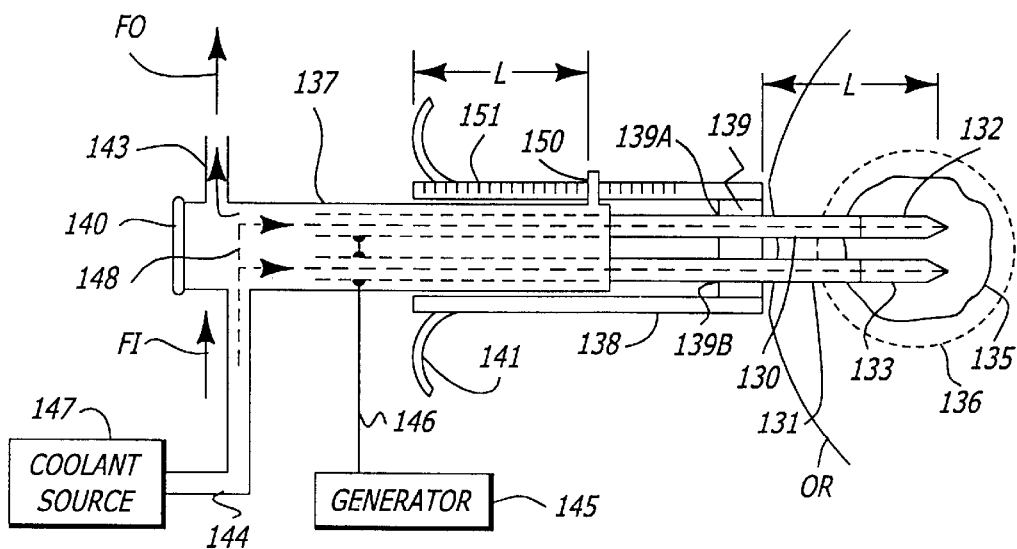
FIG. 7 shows a schematic diagram with a partial sectional view of a unitized plunger with a coherent cluster electrode system coupled to a generator and cooling system in accordance with the present invention.

Referring to FIG. 7, another embodiment of the present invention is shown. The electrode shafts 130 and 131 have exposed tips, illustrated by 132 and 133, that have sharpened points to penetrate organ OR. A targeted volume 135 may be a tumor. It is desired that a heat lesion be made to engulf the tumor and expand it to an additional margin, illustrated by the dashed line 136. The two electrodes shafts 130 and 131 may be stiff metal tubes for insertion into the body, either percutaneously or intraoperatively. The two electrodes are attached to a plunger unit 137, which in turn slides in a carrier or sheath 138. The guide bushing section 139 has guide holes 139A and 139B to guide the electrode shafts 130 and 131, respectively. The plunger hub 137 may be pushed through an opening in the carrier 138 while the end bushing 139 is in proximity to the surface of the organ OR. In this way, the carrier may be manually held to the organ surface, and the electrodes 130 and 131 pushed in unison into the tissue to show that their tips 132 and 133 reach the targeted volume 135. The plunger 137 may have a handle section 140 for enabling the surgeon to press the electrode shaft out through the bushing 139. The carrier 138 may have finger grip units or other gripping members, illustrated by 141 to apply a counter-balancing force against the plunger action 140 so as to stabilize the distal bushing end 139 against the organ surface OR. In this way, the cluster of electrodes may be inserted controllably and smoothly into the organ OR much as a syringe is used to insert a needle through the skin of a patient.

A connection 146 is shown to a power generator 145. The connection 146 may connect to the shafts 130 and 131 internally to the housing 137. Thus, both conductive, exposed tips 132 and 133 are raised to the same electric potential to induce an enlarged ablation. Coolant source 147 is shown with an inflow tube 144. Cold saline or other appropriate fluid flows through channel 144, as indicated by the arrows FI and into the tube elements 130 and 131, as illustrated by the arrows 148. The flow is channeled within the electrodes 130 and 131 to the tip ends 132 and 133. Exit flow of fluid from port 143 is illustrated by arrow FO.

In application, the device of FIG. 7 may be used for various clinical objectives. For example, a cluster of electrodes with two or more electrode elements may be used in such a configuration. The electrode tips, illustrated by 130 and 131, may be drawn back into the bushing 139. The bushing then rests against the external surface of organ OR. The housing 138 may be directed by a stereotactic frame, a frameless stereotactic navigator, or freehand, based on imaging data which reveals the position of the targeted 135 within the body. When the appropriate direction and depth of penetration L of the tips 132 and 133 has been determined, the plunger 140 may be pushed forward so that the inner hub 137 moves forward within the housing 138.

Thereby, the electrodes may be eased or advanced beyond the organ surface OR by a distance L. The degree of penetration may be evaluated and illustrated by a plunger indicator 150, which may move in the outside wall of carrier 138. The slot may have a scale, illustrated by the tick marks 150, to gauge the degree of depth L in FIG. 7.

Figure 8:
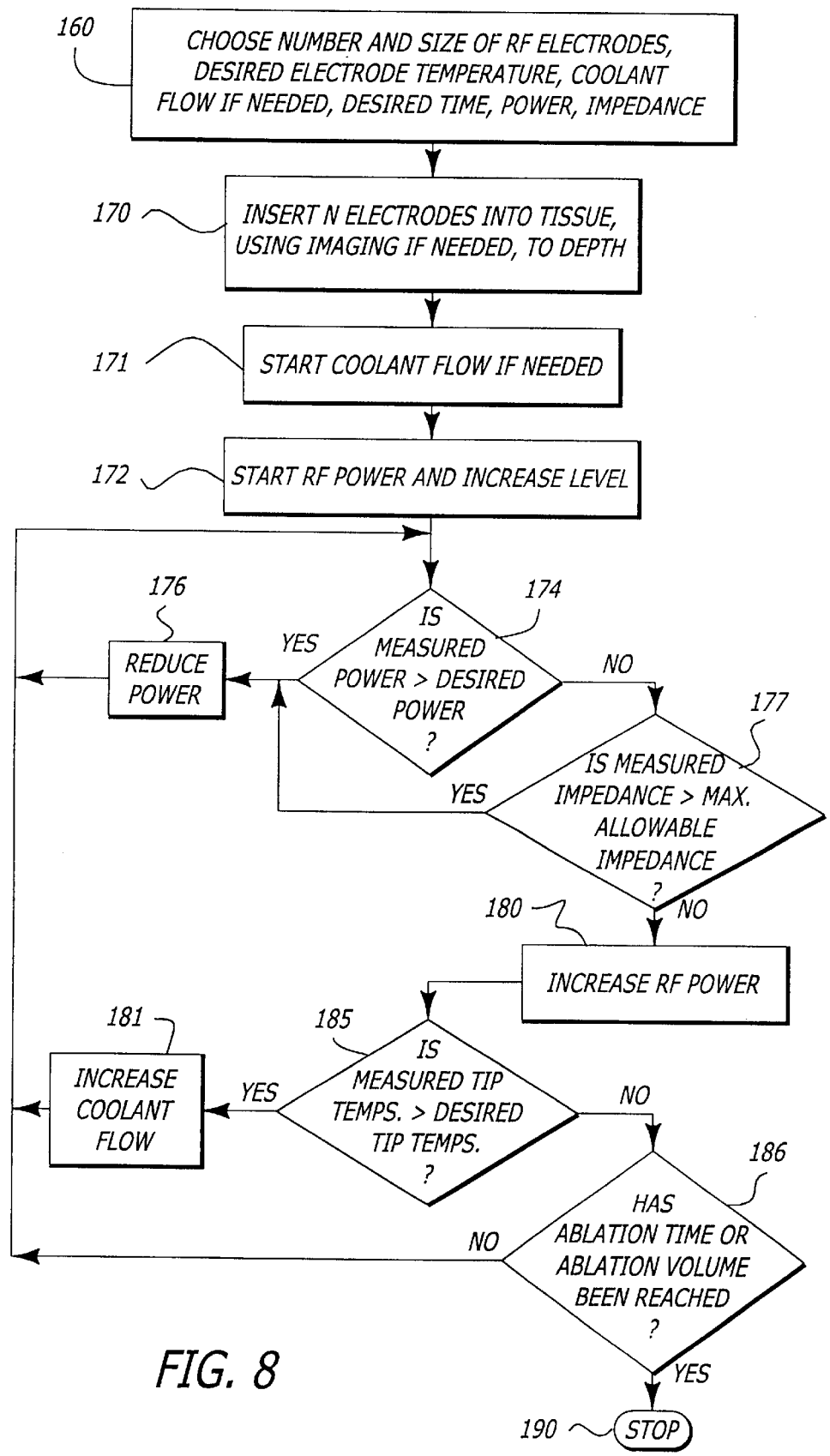
FIG. 8 shows a flow chart of the operation in accordance with the present invention.

FIG. 8 illustrates the operation of the coherent cluster electrode system in accordance with one embodiment of the present invention. At the outset, depending on the clinical conditions or requirements, an appropriate or desired configuration of the cluster electrodes is selected by the clinician. This step is generally represented by block 160. At this stage, determinations as to the following factors are considered by the clinician, which are provided by way of example: (a) the number of electrodes in the cluster; (b) their relative geometry, individual electrode sizes and tip exposures; (c) whether the electrodes are desired in one predetermined cluster or individual sizes and configurations for individual placement within the organ; (d) the determination whether cooled or non-cooled electrodes are desired. Block 160 may also represent the steps of processing image scan data from a CT, MR, ultrasound, or other type of scanner to determine the position of a targeted volume such as a tumor within the patient's body and the desired approach, placement, size, and number of electrodes. This may be done on a computer graphic workstation using 3D graphics and stereotactic orientation and methods, as illustrated by the XKnife, StereoPlan, or XSeed treatment planning systems of Radionics, Inc., of Burlington, Mass.

The stereotactic positioning of the cluster electrodes may be preplanned on the workstation. The heat isotherms and ablation volume and time-course of the ablation may be calculated and displayed on the workstation as part of the preplan. Based on historical or empirical information, the clinician may in step 160 determine the desired power to be delivered to the tissue, the temperature as measured by the electrode or measured elsewhere in the tissue by satellite temperature-sensing electrodes, the desired time duration of radiofrequency heating, and the characteristics of impedance, to determine cut-offs and control against boiling, charring, and other untoward effects. This may be done as a preplan using 3D computer graphics of the entire heating process.

The step of inserting the cluster of electrodes is represented by block 170 in FIG. 8. The cluster of electrodes may be placed individually or in unison within the body tissue, as described above. Real-time imaging may be utilized, such as ultrasound, MRI, or CT, during placement of the electrodes to determine their proper position within a targeted volume of tissue. The cluster of electrodes are inserted to a desired depth during this step. Coolant to the electrode is turned on, if required, during step 171.

The high frequency power from the external generator may be applied via the cable connection to the cluster of electrodes, either in unison or sequentially, as described above, which is represented by step 172. The level of high frequency power is increased according to empirical or preplanned parameters. This increase may be done either manually or automatically. The process may be controlled according to a microprocessor control within the generator system itself. The rise in power may be controlled according to measurement of temperature, impedance, or other feedback parameters associated with the radiofrequency lesion process.

A decision block 174 determines if the applied power to the electrodes has exceeded the desired value based on temperature monitoring or a pre-plan. If so, the power may be reduced as indicated by block 176 of the operation flow chart. If not, other parameters may be monitored, such as impedance or direct visualization of the lesion size as indicated by block 177. If these parameters, such as impedance, are within acceptable limits, power may be increased further as indicated by step 180. As indicated by step 185, the tip temperatures or temperatures from satellite probes within the tissue may be monitored. If they remain within acceptable levels or are below a targeted temperature or level, the RF power may be increased or the flow of coolant fluid, modified, as indicated by step 181.

Other criteria or parameter choices may be substituted for the steps illustrated by blocks 174, 177, 190, or 185. For example, instead of using power as the controlling parameter, the operator may measure, set, vary, or otherwise moderate the current, voltage, impedance, or temperature delivered or accomplished at each electrode. The total current level to all of the electrodes may be used as a radiofrequency output parameter to be controlled, set, or established. The current or power output to each individual electrode may be controlled or held constant. The choice of which generator output parameter is used may vary depending on the clinical need or experience of the surgeon.

The criteria for completing ablation for a set period of time is shown by step 186. If the desired lesion time or heat ablation volume is reached during step 186, the procedure may be stopped as indicated by step 190. Image monitoring or use of satellite temperature sensors may be used during step 186.

The system and process of the present invention may include other components. For example, a stereotactic frame or frameless navigator system may be used to direct and place the electrodes, which form a cluster array. An example of stereotactic frames is the CRW Stereotactic System of Radionics, Inc., of Burlington, Mass. An examples of frameless navigating stereotactic systems is the Optical Tracking System of Radionics, Inc., of Burlington, Mass. Various guide tubes, templates, holding apparatus, arc systems, spatial digitizers may be used to hold one or more of the electrodes as they are being inserted into a body or organ. Imaging modalities such as CT, MRI, ultrasound may be used before, during, or after placement of the electrodes and/or creation of the ablation lesion. One or more of the elements in a cluster electrode may have temperature-sensing within its shaft or tip. Satellite electrodes placed near the cluster electrode may be used to monitor the volumetric extent of heating. Prepared templates with multiple holes may be placed near the organ, and electrode elements of the cluster may be passed through individual holes according to a predetermined pattern.

Figure 9A:
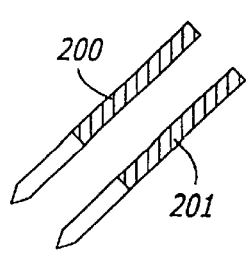
FIGS. 9a, 9b, and 9c show diagrams illustrating various parallel and non-parallel electrode tip configurations in accordance with the present invention.
Figure 9B:
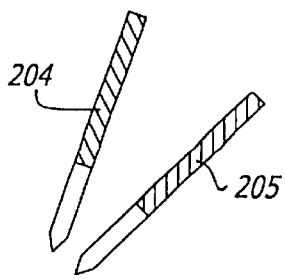
Figure 9C:
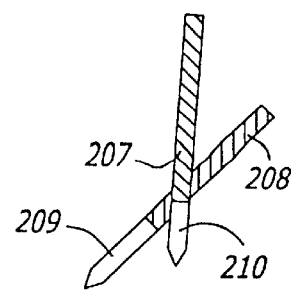

Referring to FIGS. 9a, 9b, and 9c, a variety of cluster electrode configurations are shown in accordance with the present invention. The electrodes of the cluster may be inserted into the organ in a parallel or non-parallel fashion. For example, electrodes 200 and 201 are a cluster which is inserted nearly parallel as in the discussion above. Cable connections and power source are not shown in FIG. 9, but are discussed previously. Electrodes 204 and 205 are non-parallel. When connected to the same RF voltage (potential), they will give an enlarged ablation volume. The coherent effect and increased surface area of the cluster enable more power to be put into the tissue, similar to the parallel case. Electrode array 207 and 208 are skewed and non-parallel. They, too, will enable a larger lesion volume to be made for reasons cited above. Freehand electrode insertion, percutaneously or intraoperatively, in either non-parallel or skewed geometries of electrodes, are in accordance with the present invention.

Variations in electrode placement and geometry, such as parallel or non-parallel, may be used to create changes in shape of the ablation volume as clinical needs require. Electrode insertion from varied directions may help in avoiding critical anatomical structures or obstructions while still increasing the number of electrode elements to achieve the desired lesion size. Variations in the degree of exposed conductive tip for electrode elements may vary according to a clinical targeted site. For example, in FIG. 9, exposed tip 209 has a different length from tip 210 to create a desired lesion contour. The electrodes 209 and 210 may be configured in variable lengths. This may be accomplished by using an external insulated sheath such as the shaded portion of 207 and 208, and a non-insulated inner electrode such as 209 and 210 which may be inserted into the sheaths 207 and 208. Varying degrees of insertion of the electrode will give varying lengths of conductive tip exposure. By reference, the GSK Electrode Kit of Radionics, Inc., has such variable tip exposure.

Figure 10:
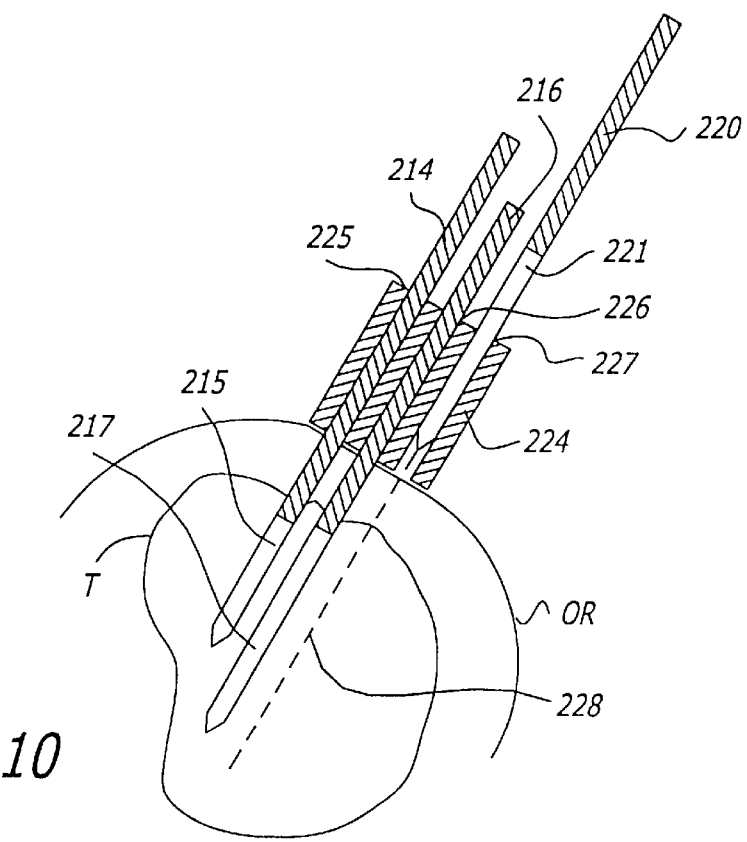
FIG. 10 illustrates a partial sectional view illustrating guided insertion of a coherent cluster electrode system in accordance with the present invention.

FIG. 10 shows another embodiment of the present invention. Three electrodes, 214, 216, and 220 are being placed into organ OR to ablate tumor T. Exposed tips 215 and 217 are the appropriate length to make a heat lesion that covers the irregular shape of tumor volume T. Electrode 220 is shown being ready to pierce organ OR. Its tip 221 is guided along the dashed line 228 to be positioned in the tumor T by the guide hole 227. They are guided in a guide block 224 which could be stereotactically placed to aim at tumor T or hand-held and aimed under ultrasound, CT, or MRI real-time monitoring as described above. Guide holes 225, 226, and 227 in block 224 are provided to plan, organize, and guide electrode insertions. They could be spaced and arranged in the guide block 224. An ultrasonic localizer, as in FIG. 1, could be connected to or be nearby block 224 for monitoring. A guide wire probe (not shown in FIG. 10) could first be placed into targeted T, and then the guide block connected to the guide block to orient the block and the guide holes. Sequential or parallel insertion of electrode arrays such as 214, 216, and 220 may be made using free hand, stereotactic, guide block, digitizer navigator, or ultrasonic, MRI, or CT control.

Figure 11:
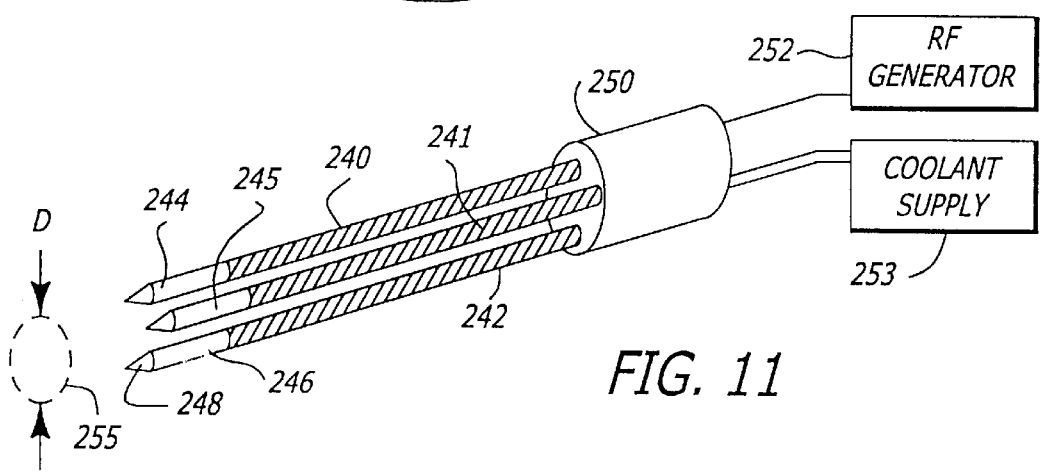
FIG. 11 shows a coherent cluster electrode system with fixed hub in accordance with the present invention.

FIG. 11 shows an example in accordance with the present invention of a cluster electrode with integral hub to fix the electrode shafts in a parallel geometry. Electrode shafts 240, 241, and 242 are rigid, elongated structures such as metal tubes. A portion of their proximal length is electrically insulated as shown by the shaded area. Each shaft has an exposed conductive tip, 244, 245, and 256, respectively. The exposed tip lengths may depend on the clinical need, and a range of lengths from 5 to 40 millimeters or more may be used. Tip diameters may range from a fraction of a millimeter to several millimeters. The tips are pointed to pierce tip as illustrated by point 248 of tip 246. The proximal ends of the shafts are fixed mechanically in hub 250 to maintain them substantially parallel. Other aspects of the electrodes are described above. Hub 250 may be adapted to be manually gripped for percutaneous introduction into the body tissue; viz. liver, brain, etc. Connection to RF generator 252 and coolant supply 253 is described in connection with the previous figures herein. The electrode shafts are in this example confined to a circular region of diameter D shown as a dotted line. For example, for electrode tips with 1 to 2 millimeter diameter, a cluster of three electrodes, as in FIG. 11, may be confined to a region diameter of 5 to 10 millimeters. The number and geometric placement of the electrode tips may vary, as described in connection with the figures above. The diameter of the electrode tips and the confinement diameter D may also vary in accordance with clinical needs.

Individual electrodes in a cluster array may or may not have pointed, with the number of electrodes in the cluster and clinical needs tissue-piercing tip, as the clinical need and technique requires. For example, in the brain, a rounded, smooth-tipped electrode will penetrate brain tissue and could provide less risk of hemorrhage from penetrating blood vessels. For percutaneous insertion, pointed electrodes or pointed guide cannulae followed by round-tipped electrodes may suit the clinical technique.

It is understood that variations in the choice of electrical output parameters from the high frequency generator to monitor or control the cluster electrode ablation process may vary widely depending on the operator's experience, technique, or preference. For example, in the embodiments above, a common RF voltage is applied to all the electrodes of the cluster simultaneously. As an alternative embodiment in accordance with the present invention, the operator may choose to control the RF current to the individual electrodes of the cluster or the total current of the cluster as a whole. Voltage variations on each electrode could be applied to achieve constant current output from each electrode. Alternatively constant power output from each electrode may be sought in some clinical settings. Voltage variations or phases between electrodes may be implemented to achieve desired temperature distribution in the tissue as monitored by temperature sensor in the tissue or by visualization of temperature distribution using thermally sensitive MRI scanning, for example. Accordingly, the choice of electrical output type, sequence, and levels and the distribution to the electrodes of the cluster should be considered to have wide variations within the scope of this invention.

In view of these considerations, as would be apparent by persons skilled in the art, implementations and systems should be considered broadly and with reference to the claims set forth below.

What is claimed is:

1. A cluster electrode instrument for use with a high frequency generator to induce coherent high frequency heat ablation volumes within targeted tissue of a patient, which comprises:

a hub; and at least three electrodes each including:

a substantially rigid elongated shaft extending from the hub and terminating in a sealed distal end section having an exposed conductive tip portion configured to be inserted into the targeted tissue and adapted at a proximal end section to be coupled to a high frequency generator to simultaneously apply an equal output voltage to each of the exposed conductive tip portions;

wherein the conductive tip portions of the at least three electrodes are arrayed relative to each other in a predetermined non-linear geometric spatial relationship relative to a longitudinal axis of the instrument such that upon application of an output voltage to the conductive tip portions, a coherent ablation isotherm is generated which encloses a desired target volume of the tissue to induce a large heat ablation volume; and a closed-loop fluid communication channel pathway which includes an inflow opening adapted for connection to a coolant fluid supply, a channel portion in fluid communication with the inflow opening, which extends distally inside the conductive tip portion to carry coolant to the inside of the conductive tip portion and further extends proximally back to an outlet opening adapted to carry coolant away from the conductive tip portion.

2. The system of claim 1, wherein the conductive tip portions of the at least three electrodes are substantially parallel, and any pair of nearest neighboring exposed, conductive tip portions of the at least three electrodes are separated by not more than 10 times the cross-sectional dimension of any of the exposed, conductive tip portions.

3. The system of claim 1, wherein the rigid, elongated shaft of each of the at least three electrodes is not more than three millimeters in diameter, and is adapted when inserted into the tissue to be positioned substantially parallel to the rigid, elongated shaft of each other of the at least three electrodes, and the rigid, elongated shaft of each of the at least three electrodes being located within a 15 mm diameter circle as defined in a plane perpendicular to a direction of the parallelity of the tip portions.

4. The system of claim 1, wherein the elongated shaft of each of the at least three electrodes comprises a metal tube which is in part insulated on its proximal end surface and wherein the exposed, conductive tip portion comprises an uninsulated distal portion of the metal tube, the metal tube being mechanically fixed to a hub at its proximal end to maintain the shaft substantially parallel to other of the electrodes and in the predetermined relationship.

5. The cluster electrode instrument of claim 1 wherein the conductive tip portions of the at least three electrodes are substantially parallel to each other.

6. A cluster electrode instrument system for use with a high frequency generator having an output voltage to induce ablation of tissues, which comprises:
   a first cluster of a plurality of electrodes adapted to be inserted into body tissue and electrically connected to the output voltage of the generator;
   a second cluster of a plurality of electrodes adapted to be inserted into the body tissue and electrically connected to the output voltage of the generator;
   the first and second clusters forming an electric current with the tissue such that electric current passes through tissue between the first and second clusters to thereby generate an ablation isotherm within the tissue;
   wherein the conductive tip portions of the electrodes of at least one of the first and second electrode clusters include a closed-loop fluid communication channel pathway which includes an inflow opening adapted for connection to a coolant fluid supply, a channel portion in fluid communication with the inflow opening, which extends distally inside the conductive tip portion to carry coolant to the inside of the conductive tip portion and further extends proximally back to an outlet opening adapted to carry coolant away from the conductive tip portion.

7. The cluster electrode instrument system of claim 6 wherein the electrodes of the first cluster include conductive tip portions arranged in substantial parallel relation.

8. The cluster electrode instrument system of claim 6 wherein the electrodes of the second cluster include conductive tip portions arranged in substantial parallel relation.

9. The cluster electrode instrument system of claim 6 wherein the conductive tip portions of the electrodes of the first cluster are arranged in a substantial linear array to define a general plate-like electrode configuration.

10. The cluster electrode instrument system of claim 6 wherein the conductive tip portions of the electrodes of the second cluster are arranged in a substantial linear array to define a general plate-like electrode configuration.

11. A system for inducing enlargement of heat ablation volumes within tissue of a patient's body, which comprises:
   a high frequency generator for supplying an output voltage; and
   at least four substantially rigid, elongated electrodes adapted to be inserted into the tissue of a patient's body, each of the at least four electrodes having exposed conductive tip portions arranged in a predetermined parallel relationship and a closed-loop fluid communication channel pathway which includes an inflow opening adapted for connection to a coolant fluid supply, a channel portion in fluid communication with the inflow opening, which extends distally inside the conductive tip portion to carry coolant to the inside of the conductive tip portion and further extends proximally back to an outlet opening adapted to carry coolant away from the conductive tip portion; and
   an electrical connection to connect simultaneously the exposed, conductive tip portions of the at least four electrodes to a desired output voltage, and the tip portions being positioned in proximity to each other when inserted into the tissue of the patient's body so that when connected to the desired output voltage, the tip portions become effectively a larger coherent electrode generating an ablation isotherm enclosing a target volume of the tissue for heat ablation of the tissue.

12. The system of claim 11 wherein the at least four electrodes arranged in an annular geometric relationship.

13. The system of claim 11 wherein the conductive tip portions of the at least four electrodes are arranged in general linear relation.

14. The system of claim 11 wherein the conductive tip portions of the at least four electrodes are arranged in general non-linear relation.

15. A process for heat ablation of tissue in a patient comprising the steps of:
   inserting at least three electrodes into the tissue in a predetermined non-linear geometric relationship relative to a plane transverse to a longitudinal axis of the electrodes, the electrodes comprising substantially rigid, elongated shafts having conductive tip portions arranged in parallel relation to each other and being adapted to penetrate tissue;
   applying substantially the same radiofrequency output through the electrodes to a targeted tissue volume to produce coherent heating of the targeted tissue volume;
   raising the radiofrequency output to a level that induces enlargement of the volume of heat ablation in the tissue near the electrodes; and
   cooling each electrode by circulating a cooling fluid through a closed-loop fluid communication channel pathway formed in each of the electrodes, which pathway includes an inflow opening adapted for connection to a coolant fluid supply, a channel portion in fluid communication with the inflow opening, which extends distally inside the conductive tip portion to carry coolant to the inside of the conductive tip portion and further extends proximally back to an outlet opening adapted to carry coolant away from the conductive tip.

* * * * *